United States Patent [19]

Kirino et al.

[11] 4,025,651
[45] May 24, 1977

[54] N-SUBSTITUTED-AMINOACETAMIDES USED AS FUNGICIDES

[75] Inventors: Osamu Kirino; Tadashi Ooishi; Nobuyuki Kameda, all of Takarazuka; Toshiro Kato, Amagasaki; Toshiaki Ozaki, Toyonaka; Akira Fujinami, Ashiya, all of Japan

[73] Assignee: Sumitomo Chemical Company, Limited, Osaka, Japan

[22] Filed: Mar. 14, 1975

[21] Appl. No.: 558,604

[30] Foreign Application Priority Data

Mar. 14, 1974 Japan .............................. 49-29731

[52] U.S. Cl. .............................................. 424/320
[51] Int. Cl.² ........................................ A01N 9/20
[58] Field of Search ............... 260/561 A; 424/320

[56] References Cited
UNITED STATES PATENTS

| | | | |
|---|---|---|---|
| 2,921,085 | 1/1960 | Schramm | 260/561 A |
| 3,223,700 | 12/1965 | Klavehn et al. | 424/320 X |

FOREIGN PATENTS OR APPLICATIONS 2,154,559  5/1973  France

*Primary Examiner*—Leonard Schenkman
*Attorney, Agent, or Firm*—Sughrue, Rothwell, Mion, Zinn & Macpeak

[57] ABSTRACT

N-substituted-aminoacetamide compounds having the formula (I)

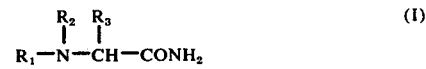

wherein $R_1$ represents a lower alkenyl group having up to 5 carbon atoms, a halogen-substituted lower alkenyl group having up to 5 carbon atoms or a lower alkynyl group having up to 5 carbon atoms, $R_2$ and $R_3$, which may be the same or different, each represents a hydrogen atom or a lower akyl group having up to 4 carbon atoms, and the inorganic and organic acid addition salts thereof, which are useful as fungicidal agents, processesfor preparing N-substituted-aminoacetamide compounds and fungicidal compositions containing at least one compound of the formula (I) as an active inredient.

8 Claims, No Drawings

N-SUBSTITUTED-AMINOACETAMIDES USED AS FUNGICIDES

BACKGROUND OF THE INVENTION

1. Field of the Invention

This invention relates to a novel class of aminoacetamide compounds. More particularly, this invention relates to a novel N-substituted-aminoacetamide compound having the formula (I)

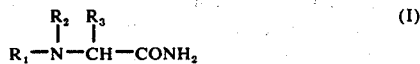

wherein $R_1$ represents a lower alkenyl group having up to 5 carbon atoms, a halogen-substituted lower alkenyl group having up to 5 carbon atoms or a lower alkynyl group having up to 5 carbon atoms, $R_2$ and $R_3$, which may be the same or different, each represents a hydrogen atom or a lower alkyl group having up to 4-carbon atoms, and the inorganic and organic acid addition salts thereof having a fungicidal activity, to a fungicidal composition comprising at least one N-substituted-aminoacetamide compound of the formula (I) above or an acid addition salt thereof, as an active ingredient, in an fungicidally effective amount, and to processes for preparing the N-aminoacetamide compound of the formula (I).

2. Description of the Prior Art

Hitherto, a wide variety of compounds having a closely related structure to the formula (I) above has been known. For example, J. Chem. Soc., 2334 (1949) discloses N-methyl-norvaleramide. However, none of the known compounds including the N-methylnorvaleramide possesses any appreciable antimicrobial activity when they are studied on their antimicrobial activities by the present inventors. As a result of further investigations, it was found that the compounds of the formula (I) above exhibit excellent antimicrobial activities due to the presence of an unsaturated substituent on the nitrogen atom.

SUMMARY OF THE INVENTION

A primary object of this invention is, therefore, to provide a novel class of N-substituted-aminoacetamides having an excellent antimicrobial, i.e., fungicidal activity.

Another object of this invention is to provide advantageous processes for preparing the N-substituted-aminpoacetamides of the formula (I).

A further object of this invention is to provide a fungicidal composition which exhibits low toxicity towards warmblooded animals, comprising at least one N-substituted-aminoacetamide compound of the formula (I).

The above and other objects of this invention will be apparent from the descriptions hereinafter given in detail.

DETAILED DESCRIPTION OF THE INVENTION

In order to accomplish these objects, the present invention provides a novel class of N-substituted-aminoacetamides of the formula (I)

wherein $R_1$ represents a lower alkenyl group having up to 5 carbon atoms, a halogen-substituted lower alkenyl group having up to 5 carbon atoms or a lower alkynyl group having up to 5 carbon atoms, $R_2$ and $R_3$, which may be the same or different, each represents a hydrogen atom or a lower alkyl group having up to 4 carbon atoms, and the inorganic and organic acid addition salts thereof.

The N-substituted-aminoacetamides of the formula (I) above can be prepared by various alternative processes and representative processes which have been found to be advantageous are hereinafter described in detail.

Process (1)

This process comprises hydrolyzing a glycinonitrile compound of the formula (II)

wherein $R_1$, $R_2$ and $R_3$ are as defined above, with an acid or a base.

Process (2)

This process comprises reacting an aminoacetate compound of the formula (III)

wherein $R_1$, $R_2$ and $R_3$ are as defined above, and $R_4$ represents a lower alkyl group, with ammonia.

Process (3)

This process comprises reacting an aminoacetamide compound of the formula (IV)

wherein $R_2$ and $R_3$ are as defined above, with a halide compound of the formula (V)

wherein $R_1$ is a defined above, and X represents a halogen atom.

Process (4)

This process which comprises reacting an amine compound of the formula (VI)

wherein $R_1$ and $R_2$ are as defined above, with a halogen compound of the formula (VII)

wherein $R_3$ is as defined above, and X represents a halogen atom.

As set forth above, the N-substituted-aminoacetamide compounds of this invention having the formula (I) are novel compounds, not previously reported in literature, and have been found to be an excellent protectant of various plant diseases. For example, the N-substituted-aminoacetamides of the present invention are useful for preventing soil-borne fungal diseases of plants. That is, the compounds of the formula (I) exhibit excellent efficacy against Fusarium wilt of tomato; yellows of Japanese radish; Fusarium wilt of cucumber; Verticillium wilt of egg-plant; yellows of strawberry; Fusarium wilt of cotton; damping-off and southern blight of vegetables; violet root rot of sweet potatoes and the like. It has also been found that the compounds of this invention exhibit remarkable efficacy against blast, Helminthosporium leaf spot, sheath blight, bacterial leaf blight, stem rot and "Bakane" disease (Gibberella fujikuroi) of rice plant; rust and smut of wheat and barley; powdery mildew, downy mildew, late blight, anthracnose, Sclerotinia rot and gray mold of agricultural and horticultural crops; brown rot of peaches; ripe rot and rust of grapes; black spot of pears; Alternaria leaf spot, scab, blossom blight of apples; scab of citrus and the like.

On further investigations of the N-substitutedaminoacetamides of the formula (I), it was unexpectedly found that these compounds exhibit a strong antimicrobial activity against microorganisms other than the pathogenic organisms in plants. That is, the compounds of this invention can be used as a rising agent in woods, bamboo wares, fibrous materials, paper materials and the like, as a hygienic additive or a preservative for industrial goods such as cosmetics, glass articles, paints, synthetic resins and the like, and as a slime inhibitor in paper mills. The utilities set forth above are completely different from the utility in the field of the agriculture and, therefore, the microorganisms in these utilities are of course different species which cause plant diseases.

The fungicidal compounds of this invention can be directly incorporated into a wide variety of materials such as fibrous materials, for example, filaments and yarns comprising cellulose, viscose, etc., materials containing synthetic resins as a base such as polyamides, polyvinyl chloride and the like, paints and lacquers containing casein, etc., inorganic or organic pigments, pastes prepared from starch or cellulose derivatives, mucilages of animal origin and oils, hair dressings for hair-curling containing polyvinyl alcohol as a base, cosmetics such as soaps, creams, ointments, body powders or dentifrices and the like. The fungicidal compounds of this invention can also be used in the form of a spray or a dry cleaner, a solution in organic solvents for impregnation of woods, or an emulsion. Further, the fungicidal compounds of this invention can be used in the form of an aqueous suspension in combination with a wetting agent or a dispersing agent for preventing putrescribed materials from the fungal infection, for example, leathers, papers, etc. The compounds of this invention are preferably used in antiinfection treatment of the rinsed materials and in treatment for preventing such materials from the attack of microorganisms. For these purposes, it is desirable to use the compounds of the formula (I) as a rinsing solution containing the compound at a concentration of 0.1 to 500 ppm, but a higher or lower concentration can also be used depending upon the utility.

The compounds of this invention are soluble in most of the organic solvents and can be dissolved in hydrophilic solvents or water-immiscible solvents such as benzene, xylene, diethyl ether, dioxane, acetone, methyl isobutyl ketone, cyclohexanone, isophorone, butyl cellosolve, dimethylformamide, dimethyl sulfoxide, acetonitrile, methylnaphthalene and the like.

In practically using the compounds of this invention, they can be used in a pure state without any inert carrier, or they can be used in combination with a carrier, a diluent or other inert agents for facilitating the application of the compounds as a fungicidal composition. The compositions comprising the compounds of this invention can be in the form of the conventional formulations, for example, dusts, wettable powders, emulsifiable concentrates (emulsions), granules, oil preparations aerosols, fine granules, fumigants, vaporizing agents and the like. The carrier which can be used in the composition can be solid, liquid or gaseous carriers. Suitable examples of the solid carriers are clay, talc, diatomaceous earth, bentonite, kaolin, acid clay, vermiculite and the like. Suitable examples of the liquid carrier include water, alcohols, ketones, benzene, xylene, toluene, solvent naphtha, petroleum ether, kerosine and the like. Suitable examples of the gaseous carriers are Freon gas, deodorized LPG, methyl chloride, vinyl chloride monomer, dimethyl ether, nitrogen, carbon dioxide and the like.

The compositions described above can be used by diluting with water or can be used per se without dilution using a technique well known in the art, for example, spraying, dusting, soil application and the like.

The composition described above comprising as an active ingredient 0.1 to 90, preferably 0.5 to 80, parts by weight of at least one N-substituted-aminoacetamide compound of the formula (I) and an inert carrier, can be employed for the purpose of practical use.

The compounds of the present invention having the formula (I) can be used in combination with other agents which are well known to have antimicrobial activities without adversely affecting the fungicidal activity of the compounds of the present invention. The agents which can be used in combination with the compounds of this invention include blasticidin S, kasugamycin, polyoxin, validamycin, cellocidin, 3-[2-(3,5-dimethyl-2-oxocyclohexyl)-2-hydroxyethyl]glutarimide, streptomycin, griseofulvin, pentachloronitrobenzene, pentachlorophenol, hexachlorobenzene, trichloronitromethane, 1,1,1-trichloro-2-nitroethane, dichlorodinitromethane, trichloronitroethylene, 1,1,2,2-tetrachloronitroethane, methylene bisthiocyanate, 2,6-dichloro-4-nitroaniline, zinc ethylene bisdithiocarbamate, zinc dimethyl dithiocarbamate, manganese ethylene bis-dithiocarbamate, bis(dimethylthiocarbamoyl)-disulfide, 2,4,5,6-tetrachloro isophthalonitrile, 2,3-dichloro-1,4-naphthoquinone, tetrachloro-p-benzoquinone, p-dimethylaminobenzenediazo sodium sulfonate, 2-(1-methylheptyl)-4,6-dinitrophenyl crotonate, 2-heptadecylimidazoline acetate, 2,4-dichloro-6-(o-chloroanilino)-s-triazine, dodecylguanidine acetate, 6-methyl-2,3-quinoxalinedithiol cyclic-S,S-dithiocarbonate, 2,3-quinoxalinedithiol cyclic trithiocarbonate, N-trichloromethylthio-4-cyclohexene-1,2-dicarboxyimide, N-(1,1,2,2-tetrachloroethylthio)-4-cyclohexene-1,2-dicarboxyimide, N-(dichlorofluoromethylthio)-N-(dimethylsulfamoyl)aniline, 1,2-bis(3-methoxycarbonyl-2-thioureido)benzene, 1,2-bis(3-ethoxycarbonyl-2-thioureido)benzene, 2-amino-1,3,4-thiadiazole, 2- amino-5-mercapto-1,3,4-thiadiazole, o-phenylphenol, N-(3,5-dichlorophenyl)maleimide, N-(3,5-dichlorophenyl)-succinimide, N-(3,5-dichlorophenyl)itaconimide, 3-(3',5'-dichlorophenyl)-5,5-dimethyloxazolidine-2,4-dione, 2,3-dihydro-5-carboxanilido-6-methyl-1,4-oxathine-4,4-dioxide, 2,3-dihydro-5-carboxanilido-6-methyl-1,4-oxathine, 1-(N-n-butylcarbamoyl)-2-methoxycarbonylaminobenzimidazole, O,O-diisopropyl-S-benzylphosphorothioate, O-ethyl-S,S-diphenylphosphorodithioate, O-butylS-benzyl-S-ethylphosphorodithioate, O-ethyl-O-phenyl-O-(2,4,5-trichlorophenyl)phosphate, O,O-dimethyl-O-(3-methyl-4-nitrophenyl)-phosphorothioate, S-[1,2-bis(ethoxycarbonyl)ethyl]-O,O-dimethylphosphorodithioate, O,O-dimethyl-S-(N-methylcarbamoylmethyl)phosphorodithioate, O,O-diethyl-O-(2-isopropyl-6-methyl-4-pyrimidyl)thiophosphate, 3,4-dimethylphenyl N-methylcarbamate, iron methylarsonate and an ammonium salt thereof, 2-chloro-4,6-bis(ethylamino)-s-triazine, 2,4-dichlorophenoxyacetic acid and salts and esters thereof, 2-methyl-4-chlorophenoxyacetic acid and salts and esters thereof, 2,4-dichlorophenyl-4'-nitrophenyl ether, sodium pentachlorophenolate, N-(3,4-dichlorophenyl)-propionamide, 3-(3',4'-dichlorophenyl)-1,1-dimethylurea, α,α,αtrifluoro-2,6-dinitro-N,N-di-n-propyl-p-toluidine, 2-chloro-2',6'-diethyl-N-(methoxymethyl)acetamide, 1-naphthyl N-methylcarbamate, methyl N-(3,4-dichlorophenyl)carbamate, 4-chlorobenzyl, N,N-dimethylthiolcarbamate, N,N-diallyl-2-chloroacetamide, O-ethyl-O-[3-methyl-6-nitrophenyl)-N-sec-butylphosphorothioamidate, S-n-butyl-S-(p-t-butylbenzyl)-N-(3-pyridyl)imidodithiocarbonate, S-n-heptyl-S-(p-t-butylbenzyl)-N-(3-pyridyl)imidodithiocarbonate and the like.

The compositions comprising at least one of the N-substituted-aminoacetamides of the formula (I) of the present invention and other agents illustrated as above are very useful for preventing simultaneously infections caused by two or more different types of pathogenic organisms and, in addition, are expected to be useful since some of the compositions exhibit a synergistic effect with respect to the activity of each component of the compositions.

Further, the compounds of the present invention can also be used in combination with other agricultural agents such as antimicrobial agents, nematocides, miticides and the like, as well as with fertilizers.

When the compounds of the present invention are used for industrial utilities, they can be employed in a pure state without inert components such as diluents, excipients, carriers, etc. and other inert additives. As is apparent to one skilled in the art, the compounds of this invention can be formulated with various inert components into a wide variety of preparations. For example, since the compounds of the present invention are soluble in most of the solvents, they can be advantageously used in the form of the solutions in such solvents. These preparations can be used for the industrial materials to be prevented from fungal infections by an appropriate technique which is well known in the art, for example, directly incorporating into such materials, or by such procedures as coating, injection or immersion.

Of the N-substituted-aminoacetamides of the present invention having the formula (I) above, particularly preferred compounds which have been found to possess a markedly high fungicidal activity are those having the following formula

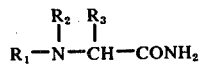

wherein $R_1$ represents an allyl group, a chloroallyl group or a propargyl group, $R_2$ represents a hydrogen atom, a methyl group or an ethyl group, and $R_3$ represents a hydrogen atom.

As described previously, the N-substituted-aminoacetamides of the formula (I) can be prepared by various processes. Typical procedures which have been found to be useful [Processes (1) to (4)] are hereinafter described in greater detail.

In the Process (1) for preparing the N-substituted-aminoacetamides of the formula (I) of the present invention, a glycinonitrile of the formula (II)

wherein $R_1$, $R_2$ and $R_3$ are as defined above, is hydrolyzed with an acid or a base. The hydrolysis can be effected by reacting the glycinonitrile of the formula (II) with an acid such as sulfuric acid, hydrochloric acid, phosphoric acid and the like, or a base such as sodium hydroxide, potassium hydroxide, barium hydroxide, ammonium hydroxide, preferably concertrated sulfuric acid, while stirring in the presence or absence of aqueous hydrogen peroxide. The reaction mixture can be optionally cooled or heated during the hydrolysis. After completion of the hydrolysis, an appropriate solvent such as methanol, ethanol, isopropanol, dioxane, tetrahydrofuran and the like, preferably ethanol, is added to the reaction mixture followed by cooling, if necessary, and isolating the precipitated crystals by, for example, filtration. The crystals thus obtained are then neutralized with an acid or a base to obtain the desired product. Alternatively, the reaction mixture obtained by the above hydrolysis can be rendered neutral with an acid or a base and extracted with an organic solvent such as methylene chloride, chloroform, acetate chlorobenzene, toluene, xylene, hexane, methyl isobutyl ketone, ethyl acetante and the like, preferably chloroform. The resulting organic layer is then dried over an appropriate dehydrating agent, for example, anhydrous sodium sulfate, anhydrous magnesium sulfate and the like and the solvent is distilled off to obtain the desired N-substituted-aminoacetamide of the formula (I) in a highly pure state and in a high yield.

Representative examples of the glycinonitrile compound which can be used as starting materials in the preparation process (1) of the present invention are given below, but the present invention is not limited to the use of these specific glycinonitrile compound.

| Glycinonitrile Compounds of Formula (II) |
|---|
| $CH_2=CH-CH_2-NH-CH_2-CN$ |
| $CH_2=CH-CH_2-NH-\underset{\underset{CH_3}{\mid}}{CH}-CN$ |
| $CH_2=CH-CH_2-NH-\underset{\underset{C_2H_5}{\mid}}{CH}-CN$ |
| $CH_2=CH-CH_2-NH-\underset{\underset{CH_2CH_2CH_3}{\mid}}{CH}-CN$ |
| $CH_2=CH-CH_2-NH-CH-CN$ |

| Glycinonitrile Compounds of Formula (II) |
|---|
| 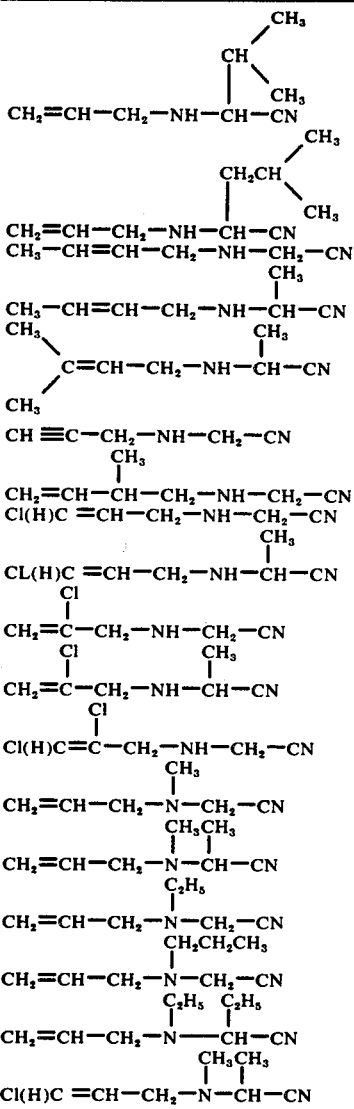 |
| 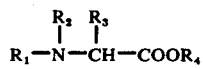 |

In the Process (2) for preparing the N-substituted-aminoacetamides of the formula (I) of the present invention, an N-substituted-aminoacetate compound of the formula (III)

$$R_1-N(R_2)-CH(R_3)-COOR_4 \quad (III)$$

wherein $R_1$, $R_2$, $R_3$ and $R_4$ are as defined above, is reacted with ammonia. This reaction can be effected by adding an aqueous ammonia or introducing ammonia gas into the N-substituted-aminoacetate compound of the formula (III) which can be optionally dissolved in a solvent, for example, benzene, chlorobenzene, toluene, xylene, ligroin, hexane, isopropyl ether, diethyl ether, tetrahydrofuran, chloroform, ethyl acetate, acetone, methanol, ethanol, isopropanol and the like, preferably ethanol. Also, the reaction mixture can be optionally cooled or heated during the reaction. After completion of the reaction the solvent used is removed from the reaction mixture by, for example, distillation, to obtain easily the desired N-substituted-aminoacetamide of the formula (I) in a highly pure state and in a high yield.

Representative examples of the N-substituted-aminoacetate compounds of the formula (III) which can be used in the Process (2) are given below, but the present invention is not limited to the use of these specific N-substituted-aminoacetate compounds.

| N-Substituted-Aminoacetamides of Formula (III) |
|---|
| 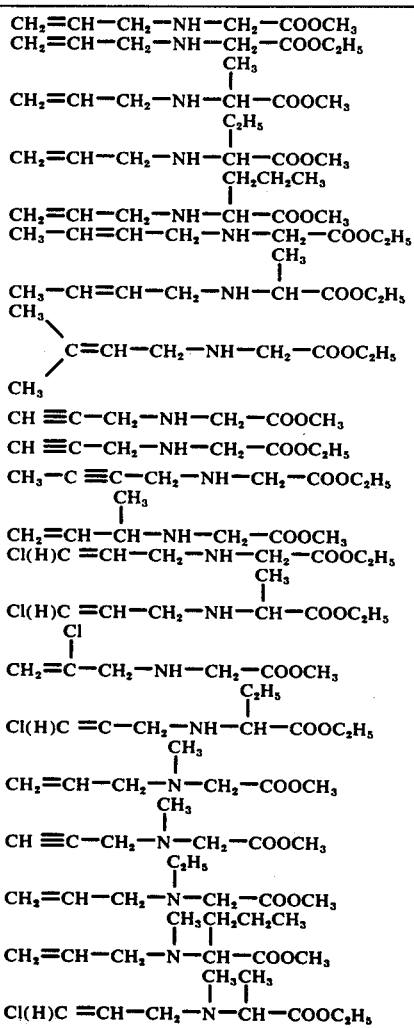 |
| 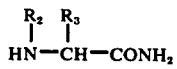 |
|  |

In the Process (3) for preparing the N-substituted-aminoacetamides of the formula (I) of the present invention, an aminoacetamide compound of the formula (IV)

$$HN(R_2)-CH(R_3)-CONH_2 \quad (IV)$$

wherein $R_2$ and $R_3$ are as defined above, with a halide compound of the formula (V)

$$R_1-X \quad (V)$$

wherein $R_1$ is as defined above. This reaction can be effected by optionally dissolving or suspending the aminoacetamide of the formula (IV) in the solvent as described for the Process (2) above, preferably ethanol, and adding dropwise the halide compound of the formula (V) to the aminoacetamide compound or a solution or suspension thereof with stirring while cooling or heating the reaction mixture. If desired, an acid acceptor such as sodium hydroxide, potassium hydroxide, sodium methylate, sodium ethylate, pyridine, triethylamine, dimethylaniline, diethylaniline and the like, preferably sodium ethylate can be added to the reaction mixture to absorb the hydrogen halide formed during the reaction. After completion of the reaction, the salt which formed was removed from the reaction mixture by, for example, filtration, and the solvent is distilled off to obtain easily the desired N-substituted-aminoacetamide of the formula (I) in a highly pure state and in a high yield.

Representative examples of the aminoacetamide compounds of the formula (IV) and the halide compounds of the formula (V) which can be used in the Process (3) are given below, but the present invention is not limited to the use of these specific compounds.

Aminoacetamide Compounds of Formula (IV)

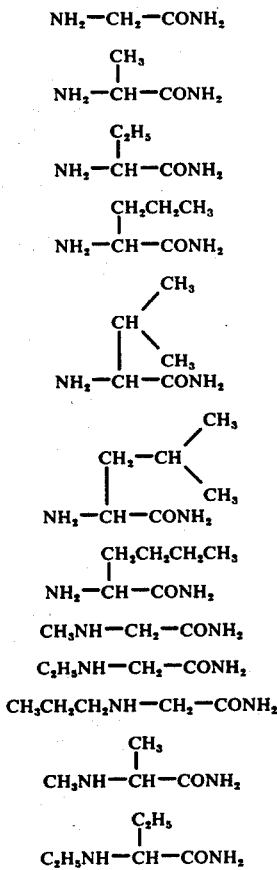

Halide Compounds of Formula (V)

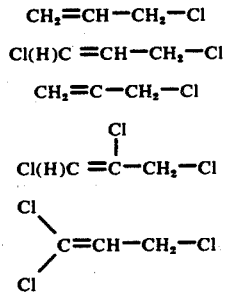

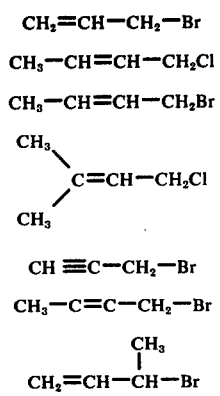

In the Process (4) for preparing the N-substituted-aminoacetamides of the formula (I) of the present invention, an amine compound of the formula (VI)

wherein $R_1$ and $R_2$ are as defined above, with a halide compound of the formula (VII)

wherein $R_3$ and X are as defined above, This reaction can be effected by optionally dissolving the amine compound of the formula (VI) in a solvent such as those described in the Process (2) above, preferably ethanol, and adding a halide compound of the formula (VII) to the amine compound of the formula (VI) or a solution thereof with stirring while cooling or heating the reaction mixture in the presence or absence of an acid acceptor as those described in the Process (3) above, preferably sodium ethylate. After completion of the reaction, the salt which formed is removed from the reaction mixture by, for example, filtration, and the solvent is distilled off to obtain easily the desired N-substituted-aminoacetamide of the formula (I) in a highly pure state and in a high yield.

Representative examples of the amine compounds of the formula (VI) and the halide compounds of the formula (VII) which can be used in the Process (4) are given below, but the present invention is not limited to the use of these specific compounds.

Amine Compounds of Formula (VI)

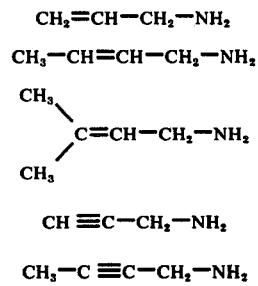

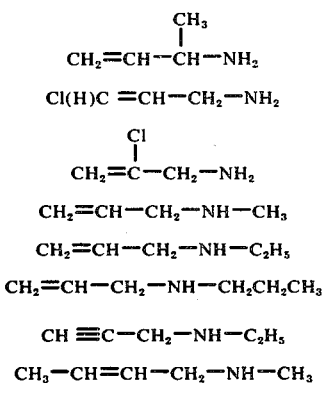

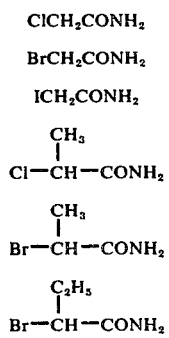

The present invention is further illustrated by the following Examples and Preparation Examples, but these examples are given for illustrative purposes only and they are not to be construed as limiting the present invention. Unless otherwise indicated, all parts, percents, ratios and the like are by weight.

EXAMPLE 1 [PROCESS (1)]

9.6 g of N-allylglycinonitrile was charged into a 100 ml four-necked flask and 15 g of concentrated sulfuric acid was added dropwise to the flask while stirring the resulting mixture at room temperature. After completion of the addition, the resulting mixture was heated at a temperature of 100° C for 1 hour. After completion of the reaction, the reaction mixture was ice-cooled and rendered neutral with a 10% aqueous sodium hydroxide solution. The mixture was then extracted 5 times with 50 ml of chloroform. The chloroform layer was dried over anhydous sodium sulfate and chloroform was distilled off under reduced pressure to obtain 7.4 g of the desired N-allylglycine amide as white crystals having a melting point of 47.5°–48° C. Elemental Analysis:

Calcd. for $C_5H_{10}N_2O$ (%): C, 52.61; H, 8.83; N, 24.54. Found: (%): C, 52.59; H, 8.77; N, 24.39.

EXAMPLE 2 [PROCESS (2)]

14.1 g of N-propargylglycine ethyl ester, 50 ml of 20% aqueous ammonia and 15 ml of ethyl alcohol were charged into a 100 ml flask and the mixture was heated under refluxing for 5 hours. After completion of the reaction, the solvent was removed by distillation under reduced pressure and the resulting residue was washed with a small amount of ethyl alcohol to obtain 9.2 g of the desired N-propargylglycine amide as white crystals having a melting point of 70°–71° C.

Elemental Analysis: Calcd. for $C_5H_8N_2O$ (%): C, 53.56; H, 7.19; N, 24.98. Found (%): C, 53.72; H, 7.03; M, 24.85.

EXAMPLE 3 [PROCESS (3)]

7.4 g of glycine amide and 6.8 g of sodium ethylate were charged into a 100 ml four-necked flask, and 30 ml of ethyl alcohol was added to the mixture. To the resulting solution was then added dropwise 13.5 g of crotyl bromide over a period of 1 hour at room temperature. After completion of the addition, the mixture was heated at a temperature of 50° C for 2 hours. After completion of the reaction, sodium bromide which precipitated upon cooling the reaction mixture was removed by filtration and the solvent was removed by distillation under reduced pressure to obtain 10.3 g of the desired N-crotylglycine amide as a pale yellow oily substance having $n_D^{23.5}$ 1.4991.

Elemental Analysis: Calcd. for $C_6H_{12}N_2O$ (%): C, 56.23; H, 9.44; N, 21.86. Found (%): C, 55.99; H, 9.31; N, 21.67.

EXAMPLE 4 [PROCESS (4)]

5.7 g of allylamine and 6.8 g of sodium ethylate were charged into a 100 ml four-necked flask, and 30 ml of ethyl alcohol was added to the mixture. To the resulting solution was then added 10.8 g of α-chloropropionamide over a period of one hour at room temperature while stirring, and the resulting mixture was heated under refluxing for 5 hours. After completion of the reaction, sodium chloride which precipitated upon cooling the reaction mixture was removed by filtration and the solvent was removed by distillation under reduced pressure to obtain 8.0 g of the desired N-allylalanine amide as white crystals having a melting point of 77.5°–78° C.

Elemental Analysis: Calcd. for $C_6H_{12}N_2O$ (%): C, 56.23; H, 9.44; N, 21.86. Found (%): C, 56.12; H, 9.38; N, 21.70.

Following the procedure as described in one of the foregoing Examples 1 to 4, the compounds shown in Table 1 below were also prepared.

Table 1

| Compound Nos. | Chemical Structure | Process Nos. | Physical Properties |
|---|---|---|---|
| (1) | $CH_2=CH-CH_2-NH-CH_2CONH_2$ | (1) | m.p. 47.5 – 48° C |
| (2) | $CH_2=CH-CH_2-NH-\underset{CH_3}{\overset{|}{CH}}-CONH_2$ | (4) | m.p. 77.5 – 78° C |
| (3) | $CH_2=CH-CH_2-NH-\underset{CH_2CH_2CH_3}{\overset{|}{CH}}-CONH_2$ | (4) | m.p. 50 – 51.5° C |
| (4) | $CH_3-CH=CH-CH_2-NH-CH_2-CONH_2$ | (3) | $n_D^{23.5}$ 1,4991 |
| (5) | $CH\equiv C-CH_2-NH-CH_2-CONH_2$ | (2) | m.p. 70 – 71° C |

Table 1-continued

| Compound Nos. | Chemical Structure | Process Nos. | Physical Properties |
|---|---|---|---|
| (6) | Cl(H)C=CH—CH$_2$—NH—CH$_2$CONH$_2$ | (2) | $n_D^{24.0}$ 1,5759 |
| (7) | CH$_2$=C(Cl)—CH$_2$—NH—CH$_2$CONH$_2$ | (2) | $n_D^{25.5}$ 1,5693 |
| (8) | CH$_2$=CH—CH$_2$—N(CH$_3$)—CH$_2$—CONH$_2$ | (2) | m.p. 49 – 50° C |
| (9) | Cl(H)C=CH—CH$_2$—N(CH$_3$)—CH$_2$CONH$_2$ | (2) | $n_D^{27.0}$ 1,5138 |
| (10) | CH$_2$=CH—CH$_2$—NHCH$_2$CONH$_2$ . HCl | (1) | m.p. 189 – 190° C |
| (11) | (CH$_2$=CH—CH$_2$—NHCH$_2$CONH$_2$)$_2$ . H$_2$SO$_4$ | (1) | $n_D^{20.0}$ 1,4978 |
| (12) | CH$_2$=CH.CH$_2$—NH.CH$_2$CONH$_2$ . CH$_3$COOH | (1) | m.p. 43 – 44° C |
| (13) | (CH$_2$=CH—CH$_2$—NH—CH$_2$—CONH$_2$)$_2$ . (COOH)$_2$ | (1) | m.p. 193 – 194° C |

The preparation examples which are suitable in practically employing the compounds of this invention are given below, but the present invention is not limited to these specific examples.

PREPARATION EXAMPLE

1. Dust

Three parts of the compound (1) and 97 parts of clay were thoroughly blended and comminuted to obtain a dust containing 3% active ingredient [Compound (1)]. In practical use, the dust thus obtained can be employed per se or can be blended with a soil prior to the application.

2. Dust

Four parts of the compound (3) and 96 parts of talc were thoroughly blended and comminuted to obtain a dust containing 4% active ingredient [Compound (3)]. In practical use, the dust thus obtained can be employed per se or can be used for coating seeds.

3. Wettable Powder

Fifty parts of the compound (4), 5 parts of a spreading agent (alkylbenzene sulfonic acid calcium salt) and 45 parts of diatomaceous earth were thoroughly blended and comminuted to obtain a wettable powder containing 50% active ingredient. In practical use, the wettable powder thus obtained can be diluted with water prior to spreading or soil application. The wettable powder can also be applied by dusting without diluting with water.

4. Emulsion

Fifty parts of the compound (1), 35 parts of xylene and 15 parts of an emulsifying agent (a polyoxyethylene phenylphenol polymer) were blended to obtain an emulsion containing 50% active ingredient. The emulsion thus obtained can be diluted with water prior to spreading.

5. Granules

Five parts of the compound (5), 93.5 parts of clay and 1.5 parts of Gosenol (a tradename, manufactured by Nippon Synthetic Chemical Industry Co., Ltd., Japan) were thoroughly blended, granulated and dried to obtain granules containing 5% active ingredient. The granules thus obtained can be employed per se.

6. Oil

A half part of the compound (2) and 99.5 parts of kerosine were blended to obtain oil containing 0.5% active ingredient. The oil thus obtained can be spread or injected as it is.

In order to determine the effect of the compounds of the present invention on the following fungal infections, comparative tests were conducted between the following compounds of the present invention and known compounds and commercially available compounds which are practically employed in the art as follows. It should be understood, however, that the following Examples are given for the illustrative purposes only and the present invention is not limited thereto.

EXAMPLE 5

Fungicidal Activity on Yellows of Japanese Radish 0.1 m² plastic vats were filled with the soil of a crop field. A pathogenic soil which had been inoculated with a culture of Fusarium oxysporum f. raphani was blended with the soil in each vat to a depth of 5 cm from the surface of the soil. Fifty seeds of Japanese radish (var., Wase-40-nichi) were sowed on the soil of each vat. An emulsion of each of the test compounds including the control compounds shown in Table 2 below which had been diluted with water was then applied to the vat by perfusion in a volume of 300 ml (at a concentration of 500 ppm of the active ingredient). After allowing the seeds to germinate and grow for a period of one month in a greenhouse, the disease sevirity was evaluated and a ratio of healthy seedlings was calculated from the following equation:

$$\text{Ratio of Healthy Seedling (\%)} = \frac{\text{Numbers of Healthy Seedlings in each Treated Vat}}{\text{Numbers of Germinated Plants in Untreated, Non-Inoculated Vat}} \times 100$$

The results obtained are shown in Table 2 below, together with the phytotoxicity observed in each vat. As is apparent from the results, the compounds of this invention exhibited excellent fungicidal activities as compared with those of the known compounds having a closely related structure and the commercially available antimicrobial agents.

Table 2

| Compounds | Concentration of Active Ingredient (ppm) | Ratio of Healthy Seedling (%) | Phytotoxicity |
|---|---|---|---|
| (1) | 500 | 100.0 | — |
| (2) | 500 | 97.3 | — |
| (3) | 500 | 92.0 | — |
| (4) | 500 | 100.0 | — |
| (5) | 500 | 99.3 | — |
| (6) | 500 | 100.0 | — |
| (7) | 500 | 99.5 | — |
| (8) | 500 | 100.0 | — |
| (9) | 500 | 91.7 | — |
| (10) | 500 | 100.0 | — |
| (11) | 500 | 98.6 | — |
| (12) | 500 | 100.0 | — |
| (13) | 500 | 99.1 | — |
| $CH_3NHCH_2CONH_2$ * | 500 | 21.3 | — |
| $CH_3NH-CH(CH_2CH_2CH_3)-CONH_2$ * | 500 | 8.0 | — |
| benzimidazole-NHCOOCH$_3$ with CONHC$_4$H$_9$(n) ** | 500 | 75.3 | — |
| Inoculated, Untreated | — | 0.0 | — |
| Non-Inoculated, Untreated | — | 100.0 | — |

* Controls described in J. Chem. Soc., 2334 (1949)
** Commercially Available Fungicide

EXAMPLE 6

Fungicidal Activity on Blast of Rice Plant

Rice plants (Var., Kinki No. 33) were grown in a pot having a diameter of 9 cm. An emulsion containing each of the test compounds including the control compounds shown in Table 3 below which had been diluted with water was sprayed to the rice plant of the four-leaf stage in a volume of 10 ml per pot. After one day of the spraying, the pot was inoculated with a spore suspension of a blast fungus (*Pyricularia oryzae*) by spray and, after 5 days inoculation, the spots due to the infection was counted to determine the fungicidal activity of each test compound. The results obtained are shown in Table 3 below. As is apparent from the results, the compounds of this invention exhibited excellent fungicidal activities as compared with the fungicidal activity of the well-known control compounds.

Table 3

| Compounds | Concentration of Active Ingredient (ppm) | Number of Spots per Leaf | Phytotoxicity |
|---|---|---|---|
| (1) | 500 | 2.1 | — |
| (2) | 500 | 6.5 | — |
| (3) | 500 | 4.8 | — |
| (4) | 500 | 3.4 | — |
| (5) | 500 | 1.8 | — |
| (6) | 500 | 4.2 | — |
| (7) | 500 | 3.0 | — |
| (8) | 500 | 6.3 | — |
| (9) | 500 | 6.2 | — |
| (10) | 500 | 2.5 | — |
| (11) | 500 | 2.9 | — |
| (12) | 500 | 2.7 | — |
| (13) | 500 | 3.1 | — |
| $CH_3NHCH_2CONH_2$ * | 500 | 98.6 | — |
| $CH_3NH-CH(CH_2CH_2CH_3)-CONH_2$ * | 500 | 112.1 | — |
| Inoculated, Untreated | — | 126.5 | — |

* Control described in J. Chem. Soc., 2334 (1949)

EXAMPLE 7

Fungicidal Activity on Powdery Mildew of Cucumber

A plant of cucumber (Var., Kaga-Aonagafushinari) was cultivated in a pot having a diameter of 9 cm and the true leaf was removed when the first true leaf became to develop. A wettable powder containing each of the test compounds including the control compounds shown in Table 4 which had been diluted with water was then sprayed to the cotyledonous leaves in a volume of 10 ml per pot. After one day of the spraying, the pot was inoculated with a spore suspension of *Sphaerotheca fuliginea* by spray and, after 14 days inoculation, the infection of the leaves was observed. The degree of infection was rated as follows. That is, the proportion of the infected area on the leaves was investigated and classified into an infection index of 0, 1, 2, 3, 4 or 5 depending upon the severity of infection as defined below. The number of leaves corresponding to each of the infection index was counted and the degree of infection was calculated by the equation given below.

| Infection Index | Degree of Infection |
|---|---|
| 0 | No fungal lesion was found on the leaves. |
| 1 | Fungal lesion up to 2% was found on the leaves. |
| 2 | Fungal lesion up to 30% was found on the leaves |
| 3 | Fungal lesion up to 60% was found on the leaves. |
| 4 | Fungal lesion up to 95% was found on the leaves. |
| 5 | Fungal lesion more than 95% was found on the leaves. |

$$\text{Degree of Infection} = \left( \frac{\text{Infection Index} \times \text{Number of Leaves}}{5 \times \text{Number of Leaves Investigated}} \right) \times 100$$

The results obtained are shown in Table 4 below. As is apparent from the results, the compounds of this invention exhibited excellent fungicidal activities as compared with the results obtained by the control compounds.

Table 4

| Compounds | Concentratin of Active Ingredient (ppm) | Ratio of Infection | Phytotoxicity |
|---|---|---|---|
| (1) | 500 | 2.5 | — |
| (2) | 500 | 7.5 | — |
| (3) | 500 | 5.0 | — |
| (4) | 500 | 2.5 | — |
| (5) | 500 | 10.0 | — |
| (6) | 500 | 6.7 | — |
| (7) | 500 | 8.0 | — |
| (8) | 500 | 11.7 | — |
| (9) | 500 | 9.0 | — |
| (10) | 500 | 3.0 | — |
| (11) | 500 | 3.5 | — |
| (12) | 500 | 2.5 | — |
| (13) | 500 | 4.0 | — |
| $CH_3NHCH_2CONH_2$ * | 500 | 87.5 | — |
| $CH_3NH-CH(CH_2CH_2CH_3)-CONH_2$ * | 500 | 95.0 | — |
| Inoculated, Untreated | — | 100.00 | — |

* Controls described in J. Chem. Soc., 2334 (1949)

EXAMPLE 8

Fungicidal Activity on Black Spot of Pear

The newly developed branches of a pear tree (var. 20-Seiki) were sprayed with a solution containing each of the test compounds including the control compounds shown in Table 5 below in a volume of 30 ml per branch. After one day of spraying, early stage leaves were cut off, and the branches were inoculated with a spore suspension of *Alternaria kikuchiana*. The inoculated branch was placed in a humid chamber and, after 7 days inoculation, the infection of the leave was investigated.

The results obtained are shown in Table 5 below. As is apparent from the results, the compounds of this invention exhibited excellent fungicidal activities as compared with the activity of the control compounds.

Table 5

| Compounds | Concentration of Active Ingredient (ppm) | Ratio of Infection | Phytotoxicity |
|---|---|---|---|
| (1) | 500 | 2.3 | — |
| (2) | 500 | 1.6 | — |
| (3) | 500 | 8.2 | — |
| (4) | 500 | 6.9 | — |
| (5) | 500 | 5.1 | — |
| (6) | 500 | 6.4 | — |
| (7) | 500 | 5.8 | — |
| (8) | 500 | 10.6 | — |
| (9) | 500 | 5.7 | — |
| (10) | 500 | 2.2 | — |
| (11) | 500 | 3.9 | — |
| (12) | 500 | 2.5 | — |
| (13) | 500 | 6.3 | — |
| $CH_3NHCH_2CONH_2$ * | 500 | 34.6 | — |
| $CH_3NH-CH(CH_2CH_2CH_3)-CONH_2$ * | 500 | 41.7 | — |
| Inoculated, Untreated | — | 47.6 | — |

* Controls described in J. Chem. Soc., 2334 (1949)

EXAMPLE 9

Experiment using White Water

Ten g of each of the Compounds (1) to (5) of the present invention was dissolved in 100 ml of water, and 5 ml of the resulting solution was diluted with 1 l of water in a white water tank in the process of the production of the ground pulp. 5 ml of the diluted solution thus obtained was further diluted with 2 l of the white water. To 100 ml of the resulting solution were then added 10 g of glucose, 1 g of peptone, 0.05 g of magnesium sulfate and 0.01 g of calcium chloride, and the mixture was heat-sterilized. The sterilized solution was then inoculated with Bacillus sp. isolated from the slime in the paper mill. Upon incubation, the solution thus inoculated was found to be completely free from growth of the microorganism.

On the contrary, the white water prepared in the same manner as above but containing no fungicidal compound of the present invention revealed an abundant growth of microorganisms upon incubation within 24 hours.

While the invention has been described with reference to specific embodiments thereof, it will be apparent to one skilled in the art that various changes and modifications can be made therein without departing from the spirit and scope of the present invention.

What is claimed is:

1. A method for preventing soil-borne fungal diseases of plants which comprises contacting the fungi with a fungicidally effective amount of at least one aminoacetamide compound of the formula

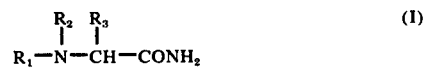

wherein $R_1$ represents a lower alkenyl group having up to 5 carbon atoms, a halogen-substituted lower alkenyl group having up to 5 carbon atoms or a lower alkynyl group having up to 5 carbon atoms, $R_2$ and $R_3$, which may be the same or different, each represents a hydrogen atom or a lower alkyl group having up to 4 carbon atoms, and an acid addition salt thereof as an active ingredient.

2. A method for preventing Fusarium wilt of tomato, yellows of Japanese radish, Fusarium wilt of cucumber, Verticillium wilt of egg-plant, yellows of strawberry, Fusarium wilt of cotton, damping-off of southern blight of vegetables, violet root of sweet potatoes, blast, Helminthosporium leaf spot, sheath blight, bacteria leaf blight, stem rot and "Bakanae" disease (Gibberella fujikuroi) of rice plant, rust and smut of wheat and barley, powdery mildew, downy mildew, late blight, anthracnose, Sclerotinia rot and gray mold of agricultural and horticultural crops, brown rot of peaches, ripe rot and rust of grapes, black spot of pears, Alternaria leaf spot, scab, blossom blight of apples or scab of citrus which comprises contacting the fungi which causes said diseases with a fungicidally effective amount of at least one aminoacetamide compound of the formula

wherein $R_1$ represents a lower alkenyl group having up to 5 carbon atoms, a halogen-substituted lower alkenyl group having up to 5 carbon atoms or a lower alkynyl group having up to 5 carbon atoms, $R_2$ and $R_3$, which may be the same or different, each represents a hydrogen atom or a lower alkyl group having up to 4 carbon atoms, and an acid addition salt thereof as an active ingredient.

3. The method for preventing soil-borne fungal diseases of plants according to claim 1, wherein in formula (I), $R_1$ represents an allyl group, a chloroallyl group or an propargyl group, $R_2$ represents a hydrogen atom, a methyl group or an ethyl group, and $R_3$ represents a hydrogen atom.

4. The method for preventing soil-borne fungal diseases of plants according to claim 1, wherein the amino acetamide compound of the formula (I) is the compound:

$$CH_2 = CH - CH_2 - NH - CH_2 - CONH_2.$$

5. The method for preventing soil-borne fungal diseases of plants according to claim 1, wherein the aminoacetamide compound of formula (I) is having the formula $$CH \equiv C - CH_2 - NH - CH_2 - CONH_2.$$

6. The method for preventing soil-borne fungal diseases of plants according to claim 1, wherein the aminoacetamide compound of formula (I) is having the formula $$Cl(H)C = CH - CH_2 - NH - CH_2 - CONH_2.$$

7. The method for preventing soil-borne fungal diseases of plants according to claim 1, wherein the aminoacetamide compound of formula (I) is having the formula $$CH_2=CH-CH_2-\underset{\underset{CH_3}{|}}{N}-CH_2-CONH_2.$$

8. The method for preventing soil-borne fungal diseases of plants according to claim 1, wherein the aminoacetamide compound of the formula (I) is having the formula $$CH_2 = CH - CH_2 - NH - CH_2 - CONH_2 \cdot NCl.$$

* * * * *